(12) United States Patent
Burrage et al.

(10) Patent No.: US 10,807,133 B2
(45) Date of Patent: Oct. 20, 2020

(54) REAL-TIME CONFIGURATION OF INSTRUMENTATION

(71) Applicant: The Government of the United States of America, as represented by the Secretary of the Navy, Arlington, VA (US)

(72) Inventors: Derek Burrage, Slidell, LA (US); Richard Crout, Slidell, LA (US); Sonia Gallegos, Slidell, LA (US); Richard W. Gould, Jr., Pearl River, LA (US); Sean C. McCarthy, Carriere, MS (US); Joel Wesson, Picayune, MS (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 494 days.

(21) Appl. No.: 15/660,920

(22) Filed: Jul. 26, 2017

(65) Prior Publication Data
US 2018/0029092 A1     Feb. 1, 2018

Related U.S. Application Data

(60) Provisional application No. 62/366,943, filed on Jul. 26, 2016.

(51) Int. Cl.
*B09C 1/00*     (2006.01)
*G06T 15/08*     (2011.01)
(Continued)

(52) U.S. Cl.
CPC .......... *B09C 1/00* (2013.01); *G01N 33/1833* (2013.01); *G06T 15/04* (2013.01); *G06T 15/08* (2013.01);
(Continued)

(58) Field of Classification Search
CPC .......... B09C 1/00; G16C 20/80; G06T 17/30; G06T 15/04; G06T 15/08; G01N 33/1833; C02F 2101/32
See application file for complete search history.

(56) References Cited

PUBLICATIONS

Fingas, M and Brown, C., Review of Oil Spill Remote Sensing, 2014, Marine Pollution Bulletin, v.83 pp. 9-23.
(Continued)

*Primary Examiner* — David P Porta
*Assistant Examiner* — Meenakshi S Sahu
(74) *Attorney, Agent, or Firm* — US Naval Research Laboratory; Will Ladd (57) ABSTRACT

Embodiments relate to instrumentation configuration for emergency response. Initially, instrument profiles are obtained from an instrument data source, where each instrument profile corresponds to an instrument for emergency response. Criteria are applied to each of the instrument profiles to determine performance scores for the instruments. Scenario sensors are used to collect real-time measurements at a geographic location of an emergency. At this stage, scenario parameters comprising the real-time measurements are obtained from a scenario data source. Each instrument profile is evaluated based on the scenario parameters to determine a suitability index. The performance score and the suitability index of each instrument profile is combined to determine an instrument rating. An instrument subset is selected from the instruments based on the instrument ratings. An instrumentation configuration for the instrument subset is generated, where the instrumentation configuration is used to deploy at least one instrument on a response vehicle or instrument platform.

20 Claims, 4 Drawing Sheets

(51) Int. Cl.
  *G06T 15/04*   (2011.01)
  *G01N 33/18*   (2006.01)
  *G06T 17/30*   (2006.01)
  *G16C 20/80*   (2019.01)
  *C02F 101/32*  (2006.01)

(52) U.S. Cl.
  CPC .............. *G06T 17/30* (2013.01); *G16C 20/80* (2019.02); *C02F 2101/32* (2013.01)

(56) References Cited

PUBLICATIONS

Fingas, M. F. and Brown, C. E., Review of Oil Spill Remote Sensing. Marine Pollution Bulletin, 1997, v. 4 No. 4, pp. 199-208, DOI:10.1016/S1353-2561(98)00023-1.

Brekke, C. and Solberg, Anne H. S., Oil spill detection by satellite remote sensing Remote Sensing of Environment, 2005 v. 95 pp. 1-13.

Jha, M. N., J. Levy and Y. Gao, Advances in Remote Sensing for Oil Spill Disaster Management: State-of-the-Art Sensors Technology for Oil Spill Surveillance Sensors, 2008, v. 8, pp. 236-2.

Puestow et al, Oil Spill Detection and Mapping in Low Visibility and Ice: Surface Remote Sensing, 2013, Arctic Oil Spill Response Technology Joint Industry Program, Final Report 5.1 pp. 83.

Leifer et al, State of the art satellite and airborne marine oil spill remote sensing: Application to the BP Deepwater Horizon oil spill., Rem. Sens. Env. 2012, v. 124, pp. 185-209.

API, Remote Sensing in Support of Oil Spill Response: Planning Guidance (American Petroleum Institute), Technical Report 1144, Sep. 2013, pp. 32.

Partington, K. An Assessment of Surface Surveillance Capabilities for Oil Spill Response using Satellite Remote Sensing, Apr. 2014, Polar Imaging Limited, Reference PIL-4000-35-TR-1.2, pp. 63.

Partington, K. An Assessment of Surface Surveillance Capabilities for Oil Spill Response using Airborne Remote Sensing, May 2014, Polar Imaging Limited, Reference PIL-4000-38-TR-1.0. pp. 82.

REAL-TIME CONFIGURATION OF INSTRUMENTATION

CROSS-REFERENCE TO RELATED APPLICATIONS

This application is a non-provisional application claiming priority to provisional application 62/366,943 filed on Jul. 26, 2016, under 35 USC 119(e). The entire disclosure of the provisional application is incorporated herein by reference.

BACKGROUND

Efficient and rapid detection of oil spills that occur over the continental shelf is vitally important for a host of societal, environmental, economic and public safety reasons. However, the variety of spill sizes and types, coupled with the dynamic environment and rapidly evolving physical and chemical characteristics of the spill and changing weather conditions, makes detection and analysis using remote sensing methods challenging. Oil spill response planners and operators have a need for up-to-date near-real time information on available and developing technologies and systems for oil spill detection and analysis. Such systems should rapidly meet their needs in a variety of spill scenarios, and under various observational conditions (including the expected meteorological and oceanographic conditions and, if known, the disposition and physico-chemical condition of the oil), as well as logistical and resource constraints.

Traditionally, the need for information on available and developing technologies has been met by a large body of published reviews, which provide useful information on the various classes and types of remotes sensing technology available for oil spill detection and analysis, but require considerable time to read and digest—time that is not available to an oil spill professional or first responder who is required to rapidly assess remote sensing options for nearly immediate deployment in order to map a rapidly evolving oil spill event.

SUMMARY

Embodiments relate to instrumentation configuration for emergency response. Initially, instrument profiles are obtained from an instrument data source, where each instrument profile corresponds to an instrument for emergency response. Criteria are applied to each of the instrument profiles to determine performance scores for the instruments and optional filters may be applied at the user's discretion. Environmental sensors are used to collect real-time measurements at a geographic location of an emergency. At this stage, scenario parameters comprising the real-time measurements are obtained from a scenario data source. Each instrument profile is evaluated based on the scenario parameters to determine a suitability index. The performance score and the suitability index of each instrument is combined to determine an instrument rating that describes both the inherent performance of that instrument, within its class, and its suitability for application to the extant spill scenario. An instrument subset is selected from among the instruments based on these instrument ratings. An instrumentation configuration for the instrument subset is generated, and this configuration is used to deploy at least one instrument on a response vehicle.

DESCRIPTION

Such published reviews as described above provide a basis and a context for developing a methodology for making up-to-date, independent assessments of modern oil spill detection and analysis technologies. The reviews also reveal the variety and dynamic nature of oil spills, the spatial and temporal behavior of oil lying on or beneath the ocean surface, and the fact that the technologies and data products used for its detection and analysis are constantly evolving. Furthermore, most current remote sensing instruments used in oil detection were designed for environmental monitoring, and are not optimized for retrieving oil spill information. Thus, it is likely that no single instrument sensor can adequately characterize a spill. In addition, sensors based on particular technologies tend to perform best under specific circumstances.

Relying exclusively on static reporting to address the requirements of the highly dynamic environmental assessment and enforcement field of oil spill response can be problematic. This difficulty can be addressed by the more dynamic approach embodied in the invention, which collects sensor information in a more readily updated data source and provides automated decision making tools to configure instrumentation.

Embodiments of the invention is to provide a methodology and computer-based system for assessing the capabilities and limitations of the current state-of-the-art oil spill detection and analysis systems for use in emergency response (e.g., offshore oil and gas operations, gas plume response, natural disaster response, etc.). The methodology allows users, such as oil spill professionals and first responders, to efficiently and rapidly configure currently available sensor technologies based on their performance and suitability for application to emergency response scenarios. It also allows users to assess the potential strengths and limitations of the sensors for that application and provides key specifications that can affect the usability of the sensors in a particular emergency response situation. A configuration tool is provided to assist the user in generating the most suitable configuration of remote sensing technology when planning remote sensing missions to detect and track, for example, a spill under prevailing geographical and weather conditions. Based on the associated data source, which can be updated as new technologies become available, embodiments also take into account the hardware features and operational requirements of the sensors, their mounting and delivery options, and where available, the associated costs for rental or purchase and installation of the sensor, or for acquisition and use of data provided by sensor owners or operators.

Some embodiments of the invention can include a user interface, which can be deployed as a desktop application or a web-based application, providing access to data sources of sensors and scenarios and allowing the user to create configurations with appropriate technologies and sensors for a particular emergency response. Such scenarios may optionally be an actual spill or a pre-defined hypothetical or historical spill.

Figure 1:
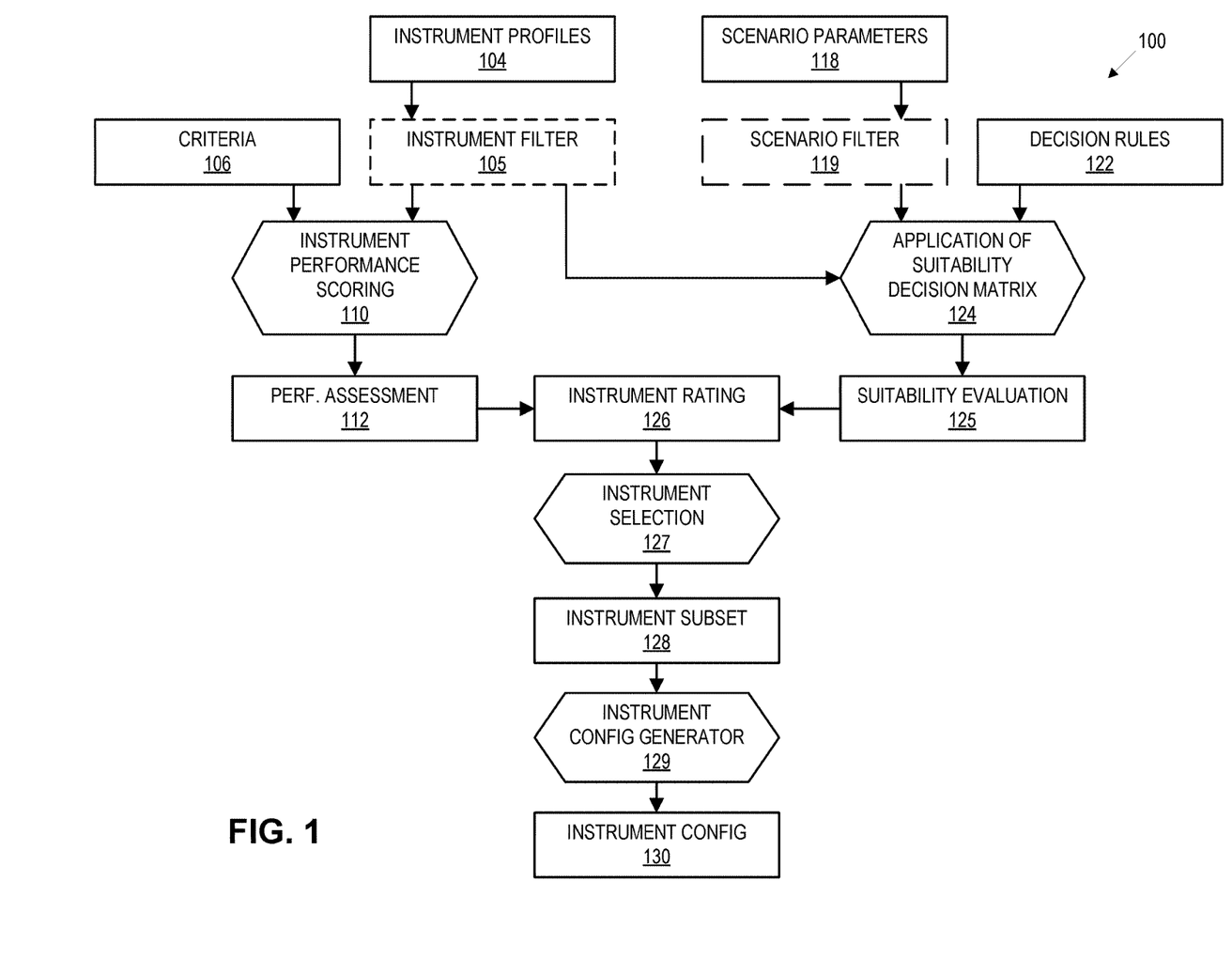
FIG. 1 shows an example workflow for real-time configuration of instrumentation.

FIG. 1 shows an example workflow 100 for real-time configuration of instrumentation. The workflow 100 performs instrumentation configuration for remote sensing technologies suitable for use during emergency response. The workflow 100 can be implemented as a sensor configuration tool which comprises a configuration application. The workflow 100 aids emergency responders in configuring instrumentation such as current oil spill detection and analysis systems that detect and analyze oil spills during offshore oil and gas operations.

Workflow 100 accesses instrument profiles 104 that describe a wide range of operational and experimental remote sensing systems that are currently in use, or under development, and criteria 106 that specify user requirements for instrumentation. In block 110, the instrument profiles 104 and criteria 106 are used to determine performance assessments 112 for potential instruments.

Instruments in instrument profiles 104 include fully operational systems, through advanced prototypes to experimental systems under development. Each instrument profile 104 is categorized as Optical, Thermal IR, or Microwave regions of the electromagnetic spectrum. Within these broad categories, instrument profiles 104 can be further distinguished between active (transmit and receive) and passive (receive only) systems. Even finer distinctions relating to wavelength and spectral resolution, temporal or spatial resolution and coverage, or technology implementation can also be incorporated into instrument profiles 104. The instrument profiles 104 can be created based on diagnostic data, historical logs, data entry, specification documents, etc. The instruments often considered for deployment during emergency response span a wide range of the E-M spectrum, instrument designs, sampling schemes, resolutions, supporting platforms and hardware implementations. These characteristics as defined in instrument profiles 104 help to determine the suitability of instruments for the intended purpose, and their performance for a given spill scenario under prevailing observational conditions. The various instruments can be placed in the following categories and sub-categories:

1) Optical (Ultra Violet, Visible and Infrared) cameras, radiometers, LIDAR's and fluorosensors, including Forward Looking Infrared Radiometers (FLIR) and Multi- and Hyper-spectral radiometers.
2) Microwave Radiometers and Radars (Side Looking Airborne Radar (SLAR), Synthetic Aperture Radar (SAR), and Marine Radar.
3) Experimental Sensors e.g., Acoustic and Nuclear Magnetic Resonance (NMR).

The instruments in instrument profiles 104 can be further categorized into Active (e.g. LIDAR, radar) and Passive (scanning, imaging and spectral radiometer) systems, and mounting platform type (surface—oil rig or ship, aerial—aircraft, aerostat or unmanned aerial vehicle (UAV), or satellite), among other classification criteria.

Optionally, instrument filter 105 can be used to filter the instrument profiles 104 before proceeding to block 110. In some cases, instrument filter 105 is specified by a user based on requirements unknown to systems performing the workflow 100. For example, a user may be aware of certain instruments being unavailable or in disrepair. In other cases, instrument filter 105 can be automatically determined based on, for example, an inventory database describing the location and quantity of instrumentation. In the cases where no instrument filter 105 is used, the full set of instrument profiles 104 can be provided to block 110.

Performance scores are determined 110 by comparing parameters of available, prototype and developing sensors (as described in instrument profiles 104 or filtered instrument profiles 105) against various criteria, using objective quantitative or qualitative measures whenever possible. In the example of oil spill response, these criteria account for the following main factors:

1) Availability (Operational or developmental status), Readiness (time to deploy) and Ownership (e.g., government agency or private contractor)
2) Spill detection potential
3) Strengths and limitations (e.g. reliability and specificity, false positives/negatives)
4) Operational and processing requirements (degree of automation, human intervention, skill levels)
5) Timeliness/data latency (real time or delayed analysis)
6) Suitability for intended use (or key parameter to be measured, e.g. thickness)
7) Hardware setup and deployment requirements
8) Mounting requirements (type of platform, mounting hardware, installation, maintenance)
9) Cost of acquisition (purchase, long-term contractor or lease, maintenance and operation)

The factors listed above fall naturally into three groups with specific implications for sensor evaluation. The first five are represented in criteria 106 that describe the expected performance of the instrument for its intended emergency response application. Accordingly, these are referred to as 'Performance Criteria'. These criteria 106 are best used to compare and rank instruments of similar class (representing where they fall in the classification scheme defined above). The criteria 106 are represented by a scoring system that ranks sensor performance against a range of possible capabilities and are also used to assess the sixth criterion, 'Suitability for Intended Use' or simply 'Suitability', as described below in block 124.

This sixth criterion represents how well the technology or sensor matches the requirements of a particular spill scenario, which can be assessed by considering the specifications of the instrument. As such, it is represented by an instrument rating 126 that aligns the conditions and requirements dictated by the factors describing the spill scenario 118 with the capabilities of the instrument. The last three criteria may be grouped as 'Deployment Criteria,' which are also used to determine the suitability of an instrument in block 124. The deployment criteria represent the effort, hardware and costs required to acquire, mount, setup and deploy the sensors. The deployment criteria can be used to determine the requirements for deploying instruments and to estimate the cost and effort required for particular sensors and configurations. The requirements and estimated cost can be strongly related to the required Instrument Platform type, which is one the Instrument specifications in the instrument profiles 104.

It should be appreciated that performance criteria 106 and suitability criteria are independent. For example, a technology, sensor or sensor suite might perform exceptionally well in situations for which it was designed, yet be quite unsuitable for the requirements of a particular spill. An obvious example is an optical sensor that operates in daylight being considered for use during a remote sensing mission to detect oil spills at night. A less obvious example is one that is prone to false positives being used to confirm that spilled oil has been successfully removed during spill mitigation operations. Instrument specifications also vary independently of the performance criteria 106 and suitability criteria, but they certainly impact both of these sets of criteria. For example, a high resolution specification might be well suited to a small scale spill, but quite unsuited to observing a large scale spill. Whether or not high resolution results in a tradeoff of reduced coverage, it could generate large volumes of data that cannot be quickly analyzed and interpreted. Hence, a low resolution sensor might be more suitable for application to a spatially extensive spill.

The sensor specifications as described in instrument profiles 104 enable comparison of the sensor technologies against the evaluation criteria discussed above. The specifications are those characteristics which may be used to succinctly describe aspects of an instrument's design and construction that together determine its performance, and along with oil scenario factors and deployment conditions, its suitability for intended use. Most, but not all, of the specifications defined in the decision tools are characteristic of each of the major classes of sensor considered in this invention. The sensor specifications are placed in convenient groups and are assigned an appropriate range of values from which the most applicable can be selected. The performance scores can be assigned to instruments in advance as the instruments are loaded into a data store as instrument profiles 104. Against these criteria 106, the performance scores (e.g., on a scale of 1-5) assigned to each technology category or sensor are used to compute a mean performance score (i.e., performance assessment 112) in block 110.

The assessment of remote sensing systems to detect and analyze oil spills is greatly facilitated by defining a set of spill scenarios that span a wide range of possible configurations for a spill. These spill scenarios may be of three types. The first and easiest to define is a scenario based entirely on the information available concerning a historical spill. If the spill was a large one, and even if it occurred before the advent of the internet, a lot of information can be gleaned about the spill characteristics and its impact. This, coupled with the known remote sensing response, is a valuable resource for sensor assessment. The second is a hypothetical spill that is configured to fill gaps in the range of historical scenarios either in geographic space or the space of the various parameters that can be used to describe a scenario. Finally, there are actual spills which are currently of concern and require a prompt remote sensing response to define its evolving characteristics. Using the old methods, a hypothetical spill has often been employed to evaluate particular sensor technologies. However the invention allows a wide range of scenarios to be evaluated quickly and the implications for sensor selection to be immediately determined.

There are several ways in which the pre-defined scenario may be used: investigations of the effectiveness of remote sensing systems and select those that are effective for particular purposes; planning purposes to help pose 'what if?' questions to guide model simulations or to provide a context for training exercises; support for decisions on advance deployment of remote sensing instrumentation in anticipation of possible future spills in particular areas or seasons; and debriefing exercises to help determine what worked and what did not, under particular spill conditions for the sensors that were deployed. For a newly-defined scenario, scenarios parameters 118 can be defined that represent the currently known characteristics of an actual evolving spill and used to help guide remediation efforts or provide a basis for ongoing remote sensing mission plans. In this case the instrumentation configuration tool can be integrated into the actual response process.

Optionally, scenario filter 119 can be used to filter the scenario parameters 118 before proceeding to block 124. In some cases, scenario filter 119 is specified by a user based on requirements unknown to systems performing the workflow 100. For example, a user may be aware of current conditions at the site of an emergency or have personal knowledge of the contents of a spill. In other cases, scenario filter 119 can automatically exclude outdated parameters based on, for example, projected parameters based an oil spill model. In the cases where no scenario filter 119 is used, the full set of scenario parameters 118 can be provided to block 124.

In the initial development of this invention, the scenarios were used to evaluate the suitability for intended purpose of each remote sensing system in the database. However, in an operational response the scenarios can be used to select/reject, or rank particular sensors for use under the prevailing spill conditions. Sensor developers may also use instrumentation configuration tools to decide for what kinds of spills a particular sensor design might be effective, or to determine which features to incorporate in a new design. In block 124, scenario parameters 118, optionally routed through scenario filter 119, are being combined with the instrument profiles 104 described above and then applied to suitability decision matrix to produce a suitability evaluation 125 representing the Suitability for Intended Use criterion, for a variety of Sensor systems. The performance assessment 112 provides a measure of the relative performance of a sensor system against criteria that are independent of its class, as well as against criteria that could be considered integral to its class. The criteria thus allow a sensor system to be ranked in terms of its overall capabilities in oil spill detection and analysis, and as well as with respect to others in its class.

The development and application of spill scenarios provides a way to assess the suitability of a particular sensor system for providing the most useful remote sensing data given the nature of the spill. In scenario parameters 118, primary characteristics of an emergency (e.g., oil spill, radiation leak, natural disaster) may be described by factors determining its timing and location, size and the type of spill/leak/disaster, weather conditions, ocean conditions, factors which might be considered to be either static (e.g., time of the initial spill) or gradually evolving (e.g., current release rate). An important secondary aspect, which can strongly affect the instrument ratings 126, is a consideration of the oceanographic and meteorological conditions prevailing, or predicted to prevail, at the time the next remote sensing survey is to be carried out. In some cases oceanographic and meteorological conditions can be obtained in real-time from pre-deployed scenario sensors. These factors, which are also considered to be characteristics of the scenario parameters 118, are much more dynamic, and can ideally be defined when sensor deployments are planned. However, the dynamic conditions can also be used for 'What-If' styles of analysis, or for sensor assessment under expected weather conditions based on the local climate. For example, if the next survey is to be carried out at night, microwave radar or thermal infrared radiometer systems would likely produce useful data, but optical systems would not. However, if it is particularly cloudy, thermal infrared (TIR) systems will also be of limited value. In clear, calm daytime conditions, optical systems will likely be most useful since microwave radar systems are particularly vulnerable to false positives when the sea is flat. If the local climate, such as in northern regions, is characterized by frequent cloud cover in addition to reduced daylight hours during winter, then forward deployment of microwave systems for the winter season is to be preferred over optical systems. The decision tools embedded in the instrumentation configuration tool help the user to determine the impact of such scenario characteristics on the suitability of the technology for application to the spill scenario.

Representative factors considered in defining various oil spills in terms of scenario parameters 118 are listed below:

Spill time and space parameters
  Discharge location
  Date and time of discharge
  Duration of discharge (e.g., <1 day is a transient discharge, 2-7 days is short-term, 1-4 weeks is medium-term, 1-12 months is long term, 1-3 years is persistent, >3 years represent a chronic discharge)
  Water body category (e.g., open sea, semi-enclosed sea, coast, lagoon, estuary, channel)
Spill size parameters
  Spill rate
  Spill volume (e.g., <10 barrels (bbl) is a micro spill, <100 bbl is very small, <1,000 bbl is small, <10,000 bbl is moderate, <100,000 bbl is medium, <1,000,000 bbl is large, <10,000,000 bbl is very large, <100,000,000 bbl is a mega spill)
Spill type parameters
  Incident type: blowout, well leak, pipeline leak, riser leak, process leak, storage tank spill, loading or unloading spill, vessel collision, shipping leak, etc.
  Oil type: light crude, heavy crude, fuel oil, etc.
  Oil condition: subsea or floating, slick or emulsion, mousse or tar, etc.

Once a spill scenario is identified, other factors that describe the spill's location in time and space are considered. These include the date and time of the event, the coordinates of the point of discharge, and the duration of the spill, indicating how long it has continued. The spill size is determined by such factors as the spill volume and discharge rate, coupled with the duration. The type of spill can be described in terms of Incident Type (e.g. blowout or ship collision) and Oil type and condition.

The range of spill scenarios defined is considered sufficient to span a broad range of locations, sizes and types, but is not unmanageably large. When descriptions of actual spill scenarios occupying significant parts of the range are available, the descriptions are used. Where there are large gaps in the range, hypothetical spill scenarios can and have been devised to represent spills of the location, type and size that have not occurred, but could conceivably occur, under circumstances that could warrant a response. This provides for a wide representative range of spill sizes and types that can be used for such applications as emergency response planning and training exercises. The spatial and temporal location of the spill is defined in three groups. The Scenario Analysis Group identifies the analyst, as well as the Date and Time applicable to the analysis. The Scenario Identification Group, and the Spill Location and Proximity to Land Group together identify the geographic location of the spill. The date and time of initial oil release is given under the Initial Release Group. Any subsequent estimates of spill size are provided in the Estimated Spill Size Group, which includes the date/time that these estimates characterized the spill. The nature of the spill and its source are described under the Spill Type and Conditions Group, which qualifies the facility or circumstances that led to the spill event, while the Initial Release Group identifies the type of structure actually discharging the oil. Under Initial Release, the spill amount and rate of release are used to characterize a sudden or a continuous discharge, or a combination of these. The Instantaneous Spill Rate factor can be revised in subsequent Analysis Events. Subsequent spill growth is tracked in the Estimated Spill Size Group by the factor Estimated Spill Volume. Under Estimated Spill Size, the Estimated Spill Volume and the Spill Area, when available, may be used to compute a mean thickness, which can be used to choose the required measurement range of instruments capable of detecting that property, and to position spill remediation or recovery equipment.

Embodiments of the invention provide a data repository of, and a systematic tool for analyzing, descriptive textual and numerical information on the oil spill sensing systems and scenarios, to assist oil spill professionals in generating instrumentation configurations in response to actual, hypothetical or historical oil spill events. The instrumentation configuration tool is designed to facilitate the subsequent assessment of sensors of various classes after generating instrument ratings 126, both to allow comparisons to be made among sensors of each class and subclass as well as the evaluation of the capability of the sensors for application to specific oil spill scenarios. For example, an effective snapshot of the current characteristics and capabilities of selected instruments 128 can be displayed and used in block 129 to generate instrumentation configurations 130. Further, embodiments are designed to be readily updateable, with procedures for the addition of new sensors and scenarios as instrumentation evolves and as new oil spill scenarios become available for scrutiny.

The instrumentation configuration tool is designed to contain, organize and give ready access to, a comprehensive data set of remote sensing systems for oil spill detection and analysis and a wide selection of historical and hypothetical oil spill scenarios with a capability for entering user-specified ones. It is also intended to provide a simple scoring system to quickly provide a convenient summary and also more detailed evaluations of the potential performance and suitability of a sensor for application to the scenario under consideration. In all cases passing, or bypassing, the optional filters, the scoring system assigns a performance score 112 of 1.00-5.00 (5.00 being the best) that represents the sensor's overall performance for oil spill applications, and a suitability index A-E (A being most suitable) that represents its suitability for application to the circumstances and conditions of a particular oil spill. This index can be combined with the performance score 112 to make an instrument rating 126 (e.g., 5A). Since the performance score 112 and suitability index are largely, but not completely independent, there is a wide range of possible combinations of the two evaluation measures. For example, an instrument might perform well in general, but be unsuited to the conditions of a particular spill, or may be well suited, based on its type, but not perform well in practice. The user should appreciate that while the resulting evaluation procedure is itself objective (based on logical decision rules 122), considerable subjective expert judgement can be used to decide what values to assign to particular sensors and criteria and how these might be ranked or scored to determine instrument performance. While these value assignments can easily be changed as new information and knowledge becomes available, such changes are best made by experts with appropriate knowledge of sensor capabilities and spill scenario parameters, to avoid biasing the decision-making process.

In some cases, the instrumentation configuration tool is used an aid to decision making. Specifically, oil spill professionals can use the tool to evaluate the available sensors and to decide which ones to deploy to detect oil spilled under particular circumstances and conditions. The quality of the evaluations will depend in part on the conceptual structure of the decision rules 122. The data sources used by the tool include information from the available published and online literature describing sensor capabilities, applications and historical spill parameters, coupled with the inventors' experience. Thus, the tool provides a valuable foundation for future development and refinement of the embodiments described herein.

The parameters in the instrument profiles 104 are used to determine the expected relative performance of instruments for use in detecting and monitoring oil spills. Performance scores 110 are assigned a score from 1 (worst) to 5 (best), representing how well the sensors are expected to perform against specific criteria. A mean score 112 (range 1.00-5.00) that represents the sum of the individual criteria scores divided by the number of criteria for each sensor can be used to rank them within particular classes or subclasses, which can then be used to determine which ones might best meet general requirements for detecting or monitoring oil spills. This mean performance score is intended to help the user answer such questions as "Which is the best Synthetic Aperture Radar (SAR) sensor to use for an oil spill survey?" where 'best' applies to that instrument which collectively meets the criteria to the greatest extent (i.e. with the highest mean performance score). In some cases, instrument parameters that are not included in the performance evaluation can be used as descriptors (or specifications) that may be useful in choosing, configuring or operating the instrument under particular circumstances.

The development of two sets of parameters 104, 118 in separate data sources, one that describes the instrument characteristics (including the specifications subset mentioned above), and a largely independent one that describes the scenarios, allows a cross-reference matrix (the 'Instrument-Scenario Matrix') to be constructed, which allows the relationship between the two sets to be specified. At the intersection of each instrument parameter (matrix column) and scenario parameter (matrix row), a decision rule 122 can be (and in more meaningful cases is) defined. In block 124, the individual decision rules 122 allow the relationship to be assigned an index (in the range A-E), that represents the suitability of the sensor for application to the scenario, with respect to that particular combination of parameter values. The ensemble of indices (represented by the sum of individual index values, divided by the number of decision rules 122 applied), or the 'suitability index' 125, also on a scale of A-E, provides an assessment of the overall suitability of use of the instrument under consideration, for application to the scenario of interest. As new information and experiences related to sensors and scenarios are accumulated, additional meaningful new decision rules 122 can be formulated in the matrix.

The performance assessment 112 and suitability evaluation 125 are combined to generate an instrument rating 126. In block 127, the instrument subset 128 can be selected from the instrument profiles 104 automatically based on the instrument rating 126. In other embodiments in block 127, the user can be presented with a report of the instrument ratings 126 and allowed to select the instruments that should be included in the instrument subset 128. After the instrument subset 128 is determined, an instrumentation configuration 130 can be generated in block 129. The instrumentation configuration 130 defines a configuration for instruments that can be implemented during an emergency response. In some cases, the instrumentation configuration 130 can be used to automatically configure the instruments (e.g., operating parameters, interoperability between instruments, etc.) in preparation of their deployment during the emergency. The instrumentation configuration can be generated based on the scenario parameters 118 and the instrument profiles 104 for the selected instruments. For example, the instrument profiles 104 can be used to tune the operating parameters of the instruments for the conditions specified in the scenario parameters 118.

Embodiments of the invention are designed to avoid the problem of information being buried in relatively inaccessible reports that take many hours to read and digest. Rather than delivering a static final report, the instrumentation configuration tool provides configurations of sensors and other devices that is based on both instrument profiles and real-time environmental data.

To contrast the embodiments of the invention with traditional methods of perusing a large body of published surveys such as the ones mentioned above, consider an oil spill analyst or respondent being asked to provide advice within the hour on what remote sensing technologies might best be applied in a newly occurring spill event. Using a traditional method, the analyst could use the limited available time to sit down and attempt to read an unspecified number of voluminous reports that contain an array of loosely related tables of information; some overly simplified, others overly complex, and none providing information in a format consistent with any other; and then decide the best sensor selection. Or, if time does not permit that, he or she could use professional judgement and experience without the benefit of up to date and comprehensive surveys to make a hasty and likely sub-optimal selection based on limited sensor information. A better alternative is for the analyst to enter the known circumstances of the spill scenario (or select a similar pre-specified scenario), combined with any available real-time data describing the observed conditions at the location, into the computer systems, and instrumentation configuration tools provided by the invention. The analyst can then rapidly and automatically select and configure preferred sensors or sensor suites based on the accumulated knowledge from all the prior sensor reviews and up-to-date sensor specifications that are contained in the data source.

Embodiments of the invention accommodate a wide range of sensor types and scenarios and provide users with a tool to rapidly configure alternative sensor technologies for a particular oil spill scenario. This allows the user to configure various sensor technologies for possible application to a wide range of spill scenarios much faster, more objectively, and with greater reliability and consistency than is possible with traditional methods. The sensors can be evaluated against historical oil spill cases that are encapsulated in the database in the form of historical scenarios. It is also possible for users to define new spill scenarios based on hypothetical or actual currently occurring spills to evaluate the suitability of the sensors described in the data base for application to such spills during future emergencies.

Embodiments efficiently utilize the information contained in published sensor technology reviews and manufacturer specification sheets, among other publically available sources, in a manner that makes it quickly and rapidly accessible by the user. The scoring approach used in the invention provides a two-part and five-point measure of both the potential performance and the suitability of the technology for an intended purpose. The performance score (1-5, with 5 representing the highest performance) allows the user to rank sensor technologies with respect to their expected performance when applied to observing situations for which they were designed. Hence, sensors in a specific category and subcategory (e.g. passive microwave instruments) can be ranked and the best performing one can be selected. The suitability index (A-E, with A representing the most suitable) is determined by cross-referencing the instruments characteristics with the oil spill characteristics. It determines the best sensor technology to use for a particular oil spill scenario. By combining these two measures, a simple two-character instrument rating can be used to determine the combined performance and suitability of a sensor. For example, a sensor rated A3 would be well suited to the purpose, but only mediocre in its class, while D5 would be poorly suited to the spill scenario despite being among the best in its class. Furthermore, embodiments allow the user to discover what characteristics of the A3 rated sensor make it a less than ideal performer, and what scenario characteristics are poorly handled by the D5 sensor.

The scoring of sensor suitability for application to particular spill scenarios is performed automatically by the sensor selection tool using a built-in decision making framework based on decision rules 122 embedded within the decision matrix 124 and relating key sensor parameters to key spill characteristics. These decision rules 122 are designed to evaluate and score the relationship between selected pairs of instrument and scenario parameter values for any combination of a specific sensor and a selected scenario, as the tool steps through the possible sensor/scenario combinations. The rules are formed by logically combining and comparing textual and numerical values using a variety of analytical tools including arithmetic inequalities, Boolean logical operations, lookup tables and a simplified form of fuzzy logic, which permits degrees of uncertainty to be effectively represented and used as a basis for decision making.

These computer systems could be used by emergency response professionals for a variety of situations and purpose such as for mission planning during an actual emergency response, for training using a simulated or hypothetical emergency scenario, for selecting technologies for routine monitoring or deployment in advance of any emergency, or for identifying gaps and deficiencies in the technologies available for detecting and analyzing spills, plumes, leaks, etc. Since time is usually a critical resource in any and all of these activities (especially during an actual emergency), the invention can allow users to rapidly and effectively obtain desired sensor configurations to make informed and timely decisions for remote sensing technology deployments.

Embodiments of the invention incorporate custom-built tools tailored to user-specified spill size and real-time environmental conditions of the spill, and the associated decision rules 122 and data base are designed for easy updating. The methods for classifying sensors and for describing their key operational features are sufficiently general and extendable to allow these tools to consider existing instruments that remotely acquire oil-related information from fixed above-surface instrument platforms such as aircraft and satellites, in situ surface-deployed remote sensing instruments, and future sensors.

Figure 2:
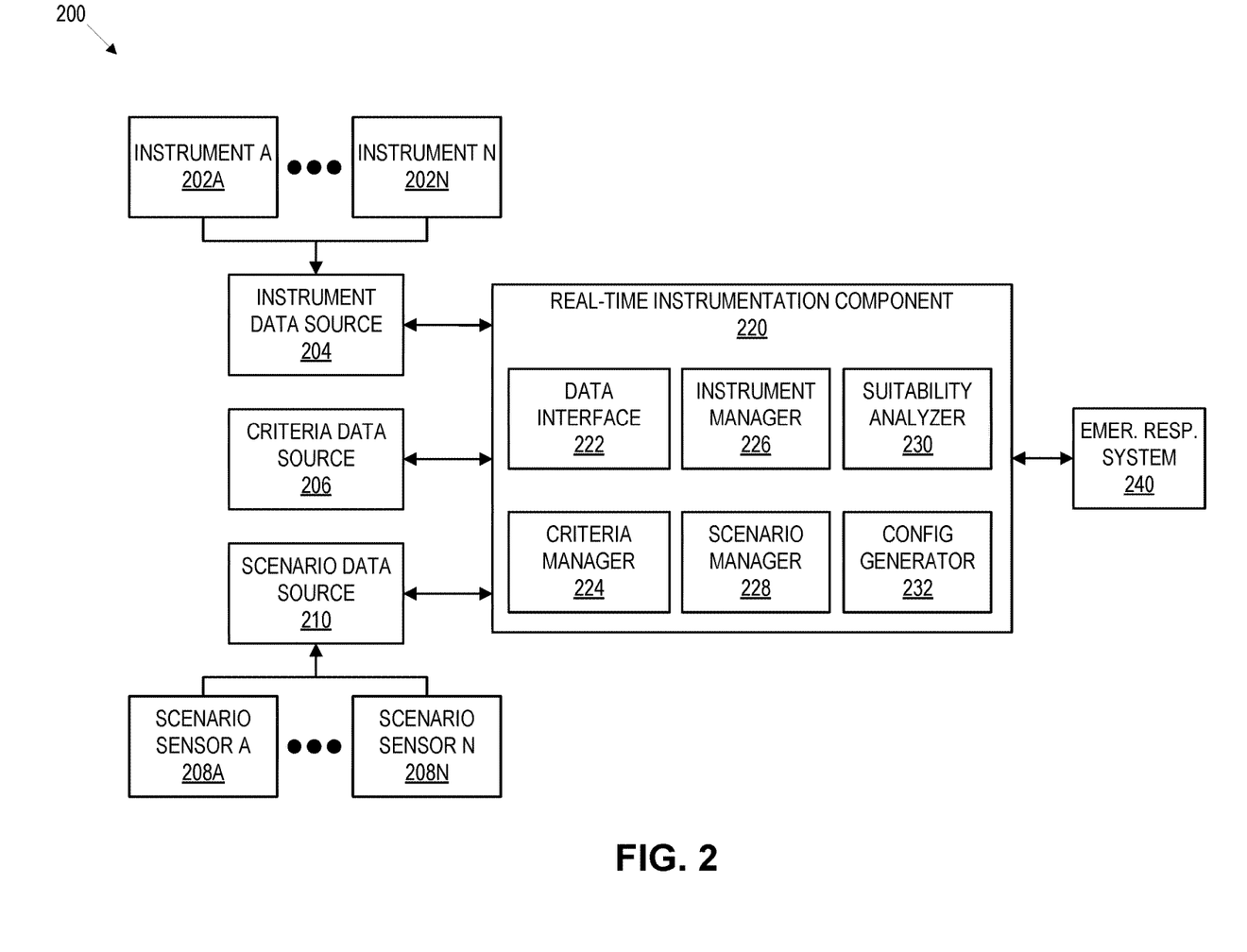
FIG. 2 shows an example system for real-time configuration of instrumentation.

FIG. 2 shows an example system 200 for real-time configuration of instrumentation. The estimation system 200 includes instruments 202A-202N, instrument data source 204, criteria data source 206, scenario sensors 208A-208N, scenario data source 210, real-time instrumentation component 220, and response vehicle 240.

Instruments 202A-202N can be a variety of sensors and sensor-related equipment that can be deployed for emergency response purposes. Examples of instruments 202A-202N include, but are not limited to, microwave and thermal infrared sensors and systems, LIDAR sensors and systems, microwave radar sensors and systems, hyperspectral radiometers, marine radar, gas correlation sensors and systems, radiation sensors and systems, etc. In some cases, instruments 202A-202N can be configured with diagnostics tools that provide performance data (e.g., specifications, firmware and degradation information, operating logs, etc.) to the instrument data source 204 for building instrument profiles as described above with respect to FIG. 1.

The data sources 204, 206, 210 stores data for access by real-time configuration component 220. Each of the data sources 204, 206, 210 can be a database, a data file, a distributed database, etc., or a combination thereof.

Instrument data source 204 stores instrument profiles for use by real-time instrumentation component 220. An instrument profile describes the characteristics of an instrument (e.g., instrument A 202A, instrument N 202N, etc.). An instrument profile can include an instrument class (e.g., passive or active and optical, microwave, acoustics, magnetic, etc.), instrument location, instrument data connection info, model number, platform type, etc. For oil spill applications, the instrument profile can also include measurement parameters such as oil spill geometry, oil type class, oil condition, oceanic parameters, atmospheric parameters, etc. The instrument profile can also include class-specific parameters such as excitation wavelength or frequency; primary, secondary, and tertiary band limits, etc.

Criteria data source 206 stores criteria for use by real-time instrumentation component 220. A criterion describes the expected performance of the instrument for its intended emergency response application, with respect to a particular feature of the instrument. Criteria can include data accessibility criteria (e.g., data access type, acquisition lead time, product delivery time, data interpreter capability, etc.), hardware accessibility criteria (e.g., sensor access type, availability, deployment planning time, deployment readiness, autonomy, etc.), instrument cost and data plan criteria (e.g., instrument cost, installation cost, initial or fixed rental, regular daily rental, etc.), etc. For oil spell applications, the criteria can also include spill sensing capability criteria (e.g., operational status, maturity, detection potential, probability of false negative, probability of false positives, etc.). Each criterion in the criteria data source 206 specifies a range of values 1-5 for performance scores, with these values ranging from lowest to highest in performance rank.

Scenario data source 210 stores scenario parameters for use by real-time instrumentation component 220. Scenario parameters describe characteristics of an emergency such as an oil spill, hazardous chemical spell, radiation leak, natural disaster, etc. For spills or explosions involving oil or other hazardous chemicals, scenario parameters can also include predicted data such as trajectory, predicted spill volume, weathering changes, etc. Scenario data source 210 can include historical scenarios, hypothetical scenarios, user-defined oil spill scenarios, and actual scenarios. Scenario parameters can also include real-time data that is collected by scenario sensors 208A, 208N.

Scenario sensors 208A, 208N are pre-deployed, in-situ sensors collecting data near or at the location of an emergency. Examples of scenario sensors 208A, 208N include, but are not limited to, weather buoys, video cameras, hazardous chemical detectors, weather radars, etc.

Real-time instrumentation component 220 provides instrument configurations based on the inherent performance of each sensor and by determining each sensor's suitability for application under different emergency response scenarios. Real-time instrumentation component 220 applies procedures to readily match pairs of sensor and scenario characteristics and apply built-in decision rules (e.g., 122 of FIG. 1) to evaluate their relationships, which aids the user in configuring appropriate technologies and sensors for deployment during such scenarios. Real-time instrumentation component 220 includes data interface 222, criteria manager 224, instrument manager 226, scenario manager 228, suitability analyzer 230, and configuration generator 232.

Data interface 222 provides real-time instrumentation component 220 with access to data sources 204, 206, 210. Data interface 222 can use various transmission technologies (e.g., wired, wireless, Internet, etc.) and protocols (e.g., web application program interface, Bluetooth protocol, database protocol, etc.) for accessing data in data sources 204, 206, 210.

Criteria manager 224 creates and accesses criteria and decision rules in criteria data source 206. Specifically, criteria manager 224 can provide a user interface that allows a user to specify criteria for various characteristics of instruments 202A-202N as well as decision rules. Criteria and/or decision rules can then be used by real-time instrumentation component 220 as described above with respect to FIG. 1.

Instrument manager 226 creates and accesses instrument profiles in instrument data source 204. Specifically, instrument manager 226 can provide a user interface that allows a user to specify/edit parameter values in instrument profiles. Instrument manager 226 can also use data collected directly from diagnostic tools of instruments 202A, 202N to create/update instrument profiles. After an instrument profile is created or updated, instrument manager 226 can also apply criteria to the instrument profile to determine performance scores for the corresponding instrument (e.g., instrument A 202A, instrument N 202N, etc.). Instrument profiles and performance scores can then be used by real-time instrumentation component 220 as described above with respect to FIG. 1.

Scenario manager 228 creates and accesses scenario parameters in scenario data source 210. Specifically, scenario manager 228 can provide a user interface that allows a user to specify/edit parameters for scenarios. Scenario manager 228 can also use data collected directly from scenario sensors 208A, 208N to create/update scenario parameters. Scenario parameters can then be used by real-time instrumentation component 220 as described above with respect to FIG. 1.

Scenario parameters, concerning spill size and type, as well as the more specific information on oil types and meteorological and oceanographic conditions can be used to provide initial inputs into an oil spill model such as the National Oceanic and Atmospheric Administration (NOAA) Automated Data Inquiry for Oil Spills (ADIOS) oil spill weathering model, or the NOAA General NOAA Operational Modeling Environment (GNOME) oil spill advection model. Such models can be used to obtain estimates of spill size early in the development of the spill, before the slick begins to break up due to air/sea interaction processes. Scenario manager 228 can also use the models to obtain estimates of likely spill size that would be useful for updating the scenario parameters when configuring instrumentation and planning initial remote sensing operations.

The ADIOS model is based, in part, on somewhat idealized spreading and dispersal mechanisms that provide valid approximations of oil spreading upon release and its weathering and dispersal (e.g., due to gravitational spreading, during the first few days of a spill). However, within about 5 days more complex ocean dispersal mechanisms, such as Stokes drift and Langmuir circulation (due to interaction of wind-waves and currents) are likely to dominate, so the model assumptions and approximations will break down. Preliminary tests performed using the ADIOS model reveal that it can provide useful estimates of spill volume and area, and of the oil spill budget. The ADIOS model is driven by specified oil type (obtainable from a comprehensive model data base), and prevailing weather conditions specified collected by scenario sensors 208A, 208N or entered by the user. Thus, it can be useful to provide scenario parameters that might not be available from in situ measurements, or previous remote sensing surveys.

The GNOME model is used by oil spill response professionals for modeling particular spills based on additional spill trajectory and weathering information obtained from supporting models as well as the results of current remote sensing surveys that would normally be ingested into the model. A supporting tool, the GNOME Online Oceanographic Data Server (GOODS), is an online tool that helps users access base maps and publically available ocean currents and winds from various models and data sources. GNOME can readily exchange files with real-time instrumentation component 220. Specifically, scenario manager can use GNOME can to determine scenario parameters based on available Geographic Information System (GIS) data. GNOME can then be used to produce an animation or successive snapshots of the oil spill trajectory as it evolves over a period of hours and days. Land boundary plots enable grounding of the spilled oil in coastal margins to be simulated by the GNOME model. Various other oil spill models could potentially be used to help specify scenarios parameters for use with the instrumentation configuration process.

A combination of ADIOS and GNOME simulation runs was conducted for a relatively small (1000 bbl) hypothetical oil spill in eastern Long Island Sound. Scenario parameters were used for model input parameters, which include spill size and date, oil type and prevailing weather conditions, among other factors, in a consistent manner for both models. This enabled the models' complementary output features to be exploited to provide a comprehensive assessment of the spill. Spill predictions were run for 1 to several days (the models impose differing limits on the forecast duration). Estimates of spill trajectory, area and length of coastline affected were made using GNOME, while ADIOS was used to provide estimates of oil spill volume and budget, taking evaporation into account.

Differences between the data requirements and capabilities of the two models were noted. For example, ADIOS allows actual crude oil of specified density and other characteristics to be specified, while GNOME allows only gross oil types to be specified. ADIOS can generate oil spill volume and track changes due to weathering; however, GNOME only provides a visual impression (map-based animation) of the spill trajectory with only a relative density indication in the form of scattered 'splots'. A very useful feature of GNOME is the provision of a 'minimum regret' solution, which represents the uncertainty associated with the primary 'best estimate' solution. In an oil grounding situation, this feature allows the likely and 'worst case' linear coastline impact to be assessed.

Scenario manager 228 can be configured to account for the strengths of, and the differences between, the different oil spill models. While the two models can be used in a complementary fashion as described above, a more comprehensive model that incorporates trajectory, weathering and spill budget information in one system could be used by scenario manager 228 to develop hypothetical spill scenarios parameters for instrument configuration.

Suitability analyzer 230 determines suitability and instrument ratings based on performance scores and scenario parameters. Suitability and instrument ratings can then be used by real-time instrumentation component 220 as described above with respect to FIG. 1.

Configuration generator 232 generates instrumentation configurations based on instrument ratings, instrument profiles, and scenario parameters. An instrumentation configuration can describe how instruments should be deployed and configured for an emergency response. After an instrumentation configuration is generated, the configuration can be directly transmitted to response vehicle(s) 240 for implementation in an emergency response. In some cases, instrument configurations can also be transmitted directly to fixed platforms (not shown) such as oil rigs, weather towers, emergency response centers, etc. for implementation in an emergency response.

As a general rule, a selected sensor will be the one with the highest suitability index that has a performance score (usually 4 or 5 in the examples use above) that would be considered adequate by the configuration generator 232. However, a user may also interact with configuration generator 232 when considering the underlying factors contributing to this rating by examining the performance scores for specific instrument profile parameters and the suitability values for specific scenario parameters and/or decision rules by examining an instrument/scenario matrix. Such considerations could suggest an alternative sensor selection. The user could also consider the relative performance of sensors falling into the same sensor class as the preferred sensor, and review the actual sensor specifications, in case there are special requirements associated with the mission that could influence the final selection of the configuration generator 232.

Configuration generator 232 may allow the user to selected pair-wise combinations of instrument and scenario parameter values for analysis. In response, real-time instrumentation component 220 automatically applies a set of decision rules (at most, one for each parameter pair) to assign suitability scores. The suitability scores can be averaged across the applicable decision rules/parameter pairs to produce a composite suitability index. This index represents the suitability of the selected instrument to provide useful oil spill remote sensing information under the circumstances of the selected scenario parameters. By clicking through various combinations of instrument and scenario, the user can determine those instruments that are best suited for application to particular emergencies. The instrument performance score can also be used to verify the likely performance of the instrument, independent of its suitability for the intended purpose.

Emergency response system 240 is configured to assist in the performance of field operations during an emergency response. Field operations can include deployment of instruments, collection of spillage, collection of data, etc. In some cases, emergency response system 240 can be located in a situation room where the field operations are planned. In other cases, the emergency response system 240 can be on a response vehicle. Response vehicles can include watercraft, aircraft, spacecraft, unmanned craft, land vehicles, etc.

Emergency response system 240 can use instrument configurations from real-time instrumentation component 220 to assist operators in installing and configuring the selected instruments for use in an emergency response. In some cases, response vehicles can be configured to directly receive and display an instrument configuration so that the configuration can be deployed on route or even at the geographic location of the emergency. In other cases, mobile devices (not shown) such as laptops, tablets, smartphones, etc. on the response vehicles can receive the instrument configurations so that the selected instruments can be deployed in a timely manner. In yet other cases, the instrument configurations can be used in situation rooms to generate plans that are provided to operators of the response vehicles. In yet other cases, the instrument configurations can be used to deploy instruments on instrument platforms such as towers, fixed or drifting weather buoys, oil platforms, etc.

Figure 3:
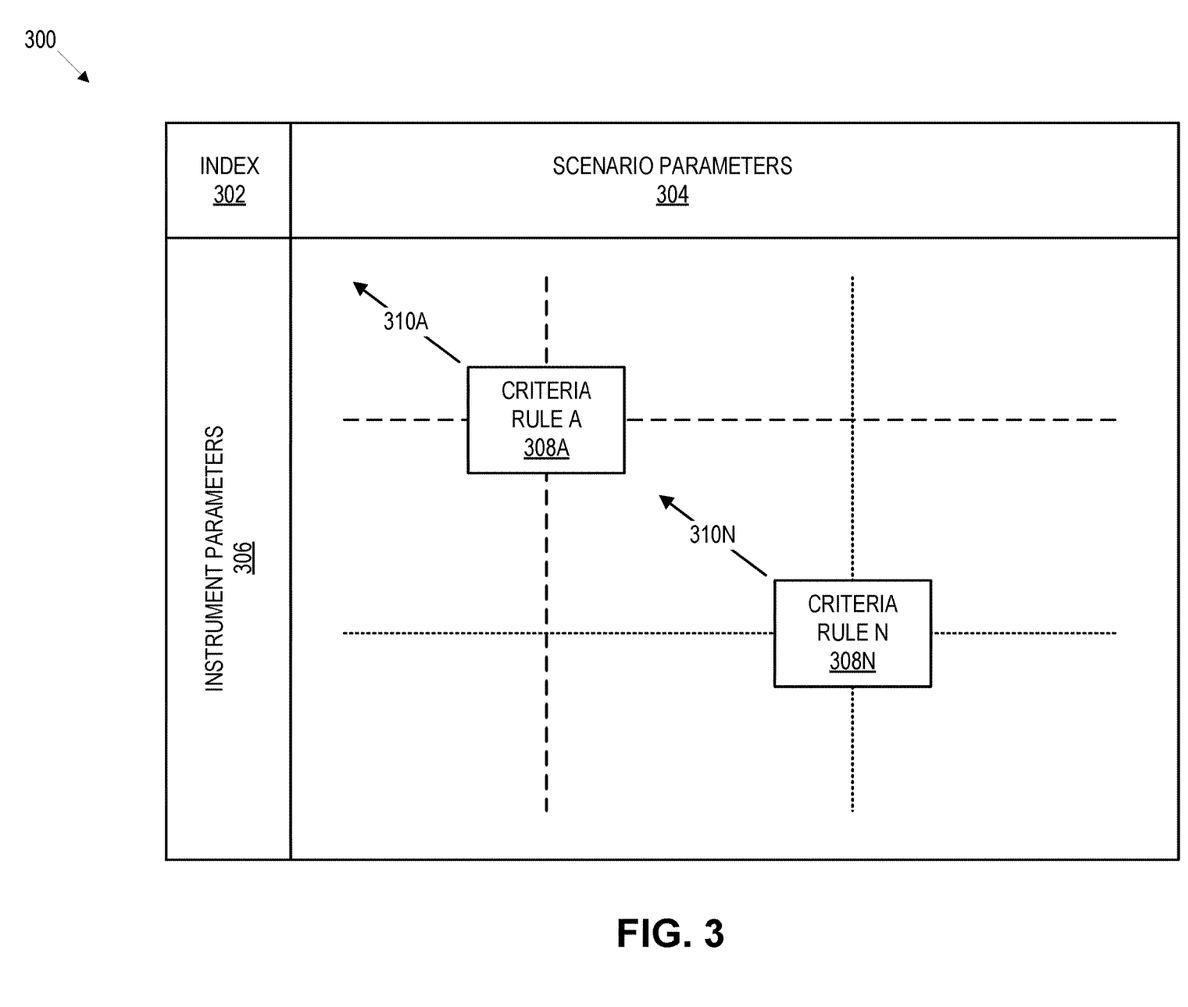
FIG. 3 shows an example instrument scenario matrix for real-time configuration of instrumentation.

FIG. 3 shows an example instrument scenario matrix 300 for real-time configuration of instrumentation. Chart E illustrates the conceptual structure of the instrument/scenario matrix 300, which incorporates decision rules 308A, 308N that relate selected pairs of scenario parameters 304 to sensor performance parameters 306. Together, these factors contribute to a suitability index 302 that combines the results of applying corresponding decision rules 308A, 308N. Each decision rule (e.g., 308A, 308N) shows a horizontal dashed line representing criteria applied to the scenario parameters 304 and a vertical dashed line presenting criteria applied to the instrument parameters 306. Acceptable index 302 values are shown by the directional arrows 310A, 310N, respectively.

The ensemble of indices (represented by the arithmetic mean of the individual raw index values), or the 'suitability index' 302, also on a decimal scale of 1.00-5.00 (or E-A), provides an assessment of the overall suitability of use of the instrument under consideration for application to the scenario of interest. This index is intended to help the user answer such questions as "Which type of instrument best meets the requirements for detecting oil, given the characteristics, and under the prevailing conditions, of a particular spill?", where 'best' applies to that instrument which is found to be most suited to that intended purpose.

The filled cells of the instrument scenario matrix 300 represent the current understanding of how sensor performance dictates suitability for intended use, with respect to a particular scenario, while the unfilled cells indicate where there is no currently known significant relationship between the relevant instrument performance parameter and scenario parameter pair.

A comprehensive survey and classification of single-band sensors, multi-band sensor packages and sensor suites, and their performance within each technology class can be leveraged to generate instrument parameters 306. The resulting metadata, including instrument specifications, performance criteria, and scores are contained in a corresponding data source. Based on these metadata, sensors can be sorted and ranked in various ways to reveal the potential performance of each instrument within its class. Historical and hypothetical spill scenarios, user-defined scenario entry, and the instrument/scenario matrix 300 allow the range of instruments available for use during particular types and sizes of spill, and the types of sensor platform and deployment mode to be evaluated. This allows the general characteristics of those classes of sensor that are best suited to these spills to be identified.

For example, the various types of spills can be conveniently classified under several broad categories by combining various combinations of values of the scenario parameters 304 discussed above with respect to FIG. 1. Size may be specified by the volume of oil spilled or by the linear dimension of the plume. The duration may be specified by the time in which oil is actually being discharged, or by the time required to complete oil recovery operations. In the categories discussed above, any combination of spill source and spill incident type is allowed.

Descriptions of spill type, platform or mission type (or sensor deployment mode), and sensor class, as defined in the scenario parameters 304 and instrument parameters 306 are employed as a basis for identifying preferred sensor types considered best suited to particular applications and conditions. For each preferred sensor system, the specifications and criteria encapsulated in the instrument parameters 306 describe the capabilities that make it one of the better performers in its class, or one that is best suited for application to the type of spill and prevailing conditions. A particular instrument selected under given conditions and with the available resources or imposed constraints may differ from another instrument chosen based on the instrument performance scores either for technical or logistical reasons. The performance scores are based on criteria related to the design, availability and operation of the sensor and are used to assess sensor performance in the context of oil spill detection and analysis; however, the performance scores do not depend on the specific characteristics of a spill (i.e., scenario parameters 304) and are not intended to indicate performance for other applications. In contrast to the performance score, the suitability index assigned to a sensor depends strongly on characteristics of the particular spill scenario (i.e., scenario parameters 304), such as spill size, time, and location, and the suitability index can change significantly from spill to spill.

Decision rules 308A, 308N are designed to evaluate and score the relationship between selected pairs of instrument and scenario parameter values for any combination of a specific sensor and a selected scenario. For example, the decision rules 308A, 308N can be applied as the user steps through the possible sensor/scenario combinations. The rules are formed by combining textual and numerical values in various ways using a variety of analytical tools such as arithmetic inequalities, Boolean logical operations, lookup tables, and a simplified form of Fuzzy logic (which being many valued, rather than merely true or false, admits the possibilities of partial truth). Each decision rule (e.g., 308A, 308N) can be characterized by the relevant sensor and scenario input parameters and their possible values, intermediate parameter values derived from relevant logical or arithmetic operations, the final decision logic that determines the suitability index value in the range 1-5 (or assigns a missing value if there is insufficient information to make a decision), the assignment of a suitability index value represented by one of the letters E-A, and a corresponding color.

In one example, a decision rule (e.g., 308A, 308N) can assign a suitability index value 302 based on the degree to which the scenario country location corresponds with the country location of the instrument, noting that a satellite sensor that orbits the entire globe is considered the most readily available and is given the value global and is assigned the highest possible composite score (5 or A (Green)). In this example, an instrument that is located in a different continent than the emergency is considered less accessible and, therefore, less suitable for application to that emergency.

In another example, a decision rule (e.g., 308A, 308N) can assign a suitability index value 302 based on the suitability of the sensor category for the season of the year in which the remote sensing mission is to be performed. In this example, the restrictions can be applied to optical sensors, which cannot be used at night and cannot generally penetrate cloud or rain. Optical sensors are therefore less useful in most parts of the world during winter, when clouds are prevalent. There are potential dependencies on latitude that can also be taken into account. Specifically, the tropics and sub-tropics may be subject to cloud and rain in the summer and the higher latitudes have greater cloud cover and few hours of daylight in winter. Both these factors would reduce the utility of optical sensors. Furthermore, active optical sensors such as LIDAR's could work at night, but might have limited capability to penetrate cloud and/or rain. The possibility that higher microwave-band sensors might have difficulties penetrating rain or fog is a further complication that can be taken into account.

In yet another example, a decision rule (e.g., 308A, 308N) can be applicable to a specific type of instrument. For instance, the decision rule (e.g., 308A, 308N) can consider the susceptibility of active microwave sensors (various types of side looking radar including SAR, SLAR, scatterometers, among others) to false positive or false negative oil spill detections as a function of surface roughness, which is most closely associated with wind speed. In relatively calm conditions, there is a higher likelihood of false detections due to the appearance of locally calm waters, or waters that are smoothed by the tendency of organic plumes (as well as oil slicks) to suppress wave action. These appear as dark returns from calm waters when, in the case of side looking instruments, the transmitted signal is spectrally reflected away from the receiver. During rough conditions (and hence moderate wind speeds) diffuse backscatter makes the surface appear brighter, unless oil suppresses this effect, in which case it can be reliably detected. These conditions tend to be optimal for oil spill detection using active radar. In storm conditions under stronger winds oil slicks, though present, are likely to be mixed downward into the subsurface. This increases the likelihood of false negative detection of oil slicks. The likelihood of false positive and false negative detections as a result of roughness variations is lower for optical instruments, which generally have a capability to distinguish target slicks spectrally. The possibility that sun glint will either aid or interfere with passive optical and microwave observations can also be taken into account. This effect would also be dependent on surface roughness as well as the view angle, latitude, time of day and season of year (which together effect sun angle). In this example, wind speed range determines the roughness conditions, where optimal wind speeds for SAR oil spill detection are 1.5 to 10 m/s. Based on the wind speed range, radars susceptible to false positives and negatives can be categorized as (1) high likelihood of ambiguous detection (false positives likely); (2) suitable conditions for unambiguous detection; (3) optimal conditions for unambiguous detection; (4) low likelihood of detection (false negatives likely); or (5) highly unlikely such as in storm or hurricane conditions (oil strongly dispersed into sub surface layers).

Figure 4:
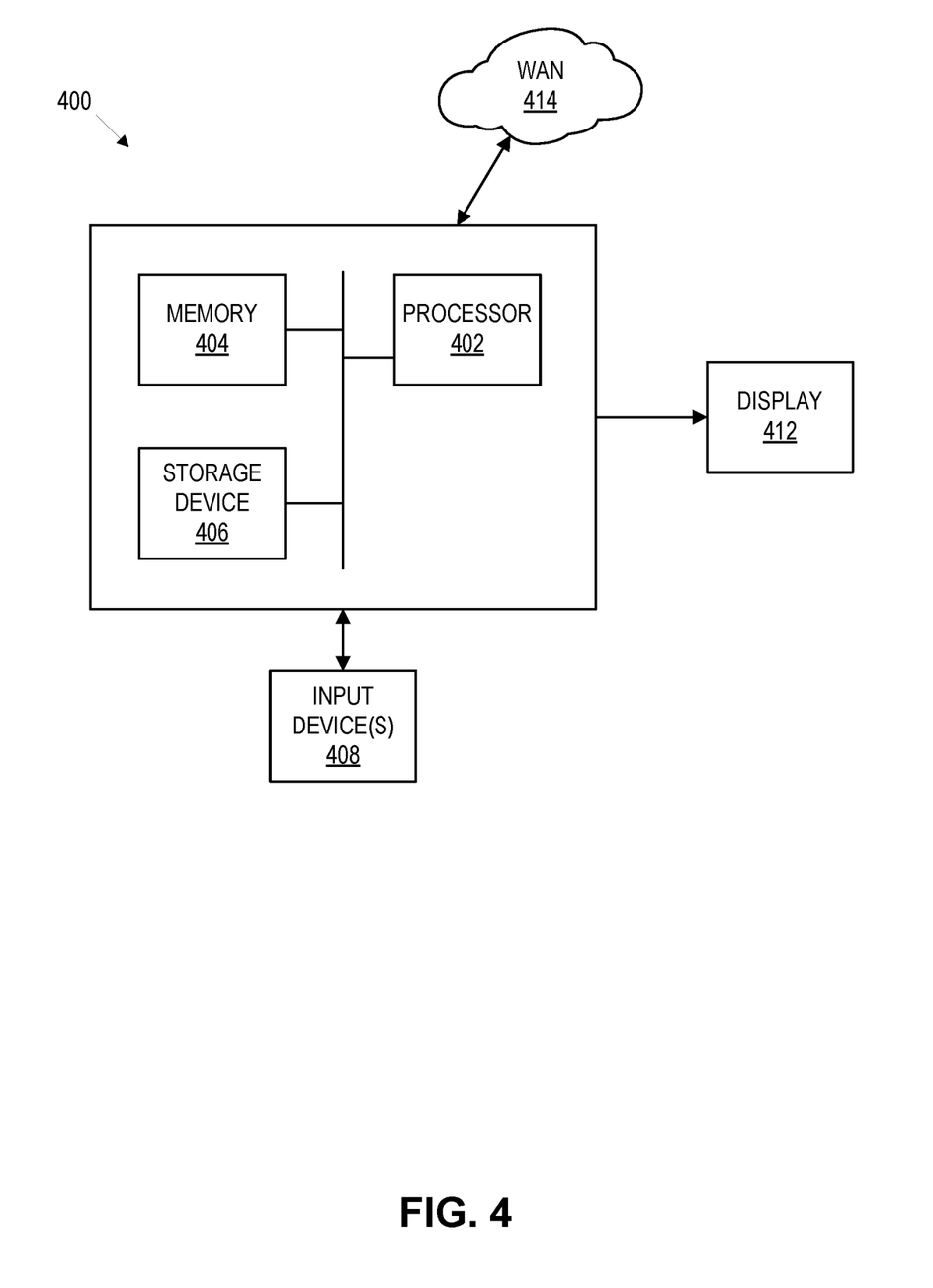
FIG. 4 shows a diagram of an example computer system for performing real-time configuration of instrumentation.

The invention or portions of the invention may be implemented on virtually any type of computer regardless of the platform being used. For example, as shown in FIG. 4, a computer system 400 includes a processor 402, associated memory 404, a storage device 406, and numerous other elements and functionalities typical of today's computers (not shown). The computer 400 may also include input means 408, such as a keyboard and a mouse, and output means 412, such as a monitor. The computer system 400 may be connected to a local area network (LAN) or a wide area network (e.g., the Internet) 414 via a network interface connection (not shown). Those skilled in the art will appreciate that these input and output means may take other forms.

Further, those skilled in the art will appreciate that one or more elements of the aforementioned computer system 400 may be located at a remote location and connected to the other elements over a network. Further, the invention may be implemented on a distributed system having a plurality of nodes, where each portion of the invention (e.g., real-time instrumentation component, response vehicle(s), data sources, etc.) may be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions to perform embodiments of the invention may be stored on a computer readable medium such as a compact disc (CD), a diskette, a tape, a file, or any other computer readable storage device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A method for instrumentation configuration for emergency response, the method comprising:
   obtaining a plurality of instrument profiles from an instrument data source, wherein each of the plurality of instrument profiles corresponds to one of a plurality of instruments for the emergency response;
   applying a plurality of criteria to each of the plurality of instrument profiles to determine a plurality of performance scores for the plurality of instruments;
   using a plurality of scenario sensors to collect real-time measurements at a geographic location of an emergency;
   obtaining scenario parameters from a scenario data source, wherein the scenario parameters comprise the real-time measurements;
   evaluating each instrument profile in the plurality of instrument profiles based on the scenario parameters to determine a suitability index for the instrument profile, wherein evaluating each instrument profile comprises evaluating each instrument profile based on parameters from a prior emergency and parameters from a simulated emergency;
   combining the performance score and the suitability index of each instrument profile in the plurality of instrument profiles to determine an instrument rating for the instrument profile;
   selecting an instrument subset from the plurality of instruments based on the instrument rating instrument rating of each instrument profile in the plurality of instrument profiles; and
   generating an instrumentation configuration for the instrument subset based on the plurality of instrument profiles and the scenario parameters, wherein the instrumentation configuration is used to deploy at least one instrument in the instrument subset on a response vehicle or instrument platform.

2. The method of claim 1, wherein the instrument rating aligns conditions and requirements specified by the scenario parameters with capabilities of the instrument subset.

3. The method of claim 1, wherein the emergency is an oil spill, and wherein the response vehicle or the instrument platform is capable of deploying or carrying and operating the at least one instrument.

4. The method of claim 3, further comprising:
   generating an oil spill trajectory by using the scenario parameters to perform an oil spill simulation; and
   updating the scenario parameters based on the oil spill trajectory.

5. The method of claim 1, wherein an instrument of the plurality of instruments comprises a diagnostic tool for providing specifications and log data of the instrument, wherein the method further comprises obtaining the specifications and the log data from the instrument, wherein the specifications and the log data are used to generate a corresponding instrument profile of the plurality of instrument profiles.

6. The method of claim 1, wherein the instrument configuration is transmitted directly to the response vehicle or instrument platform so that the at least one instrument can be configured during field operations of the emergency response.

7. A method, comprising:
   receiving a plurality of real-time measurements at a geographic location of an emergency;
   determining a plurality of performance scores for a plurality of instruments for an emergency response;
   determining a plurality of suitability indices for the plurality of instruments, wherein determining the plurality of suitability indices comprises evaluating each instrument in the plurality of instruments based on parameters from a prior emergency, parameters from a simulated emergency, and parameters from the plurality of real-time measurements; and
   determining respective instrument ratings for the plurality of instruments based on the performance scores and the suitability indices for each instrument.

8. The method of claim 7, wherein determining the plurality of performance scores comprises determining availability, readiness, and ownership of each instrument in the plurality of instruments.

9. The method of claim 7, wherein determining the plurality of performance scores comprises determining false positive and false negative potential of each instrument in the plurality of instruments.

10. The method of claim 7, wherein determining the plurality of performance scores comprises determining a degree of automation of each instrument in the plurality of instruments.

11. The method of claim 7, wherein determining the plurality of performance scores comprises determining latency of each instrument in the plurality of instruments.

12. The method of claim 7, wherein determining the plurality of performance scores comprises determining mounting requirements of each instrument in the plurality of instruments.

13. The method of claim 7, wherein determining the plurality of suitability indices comprises determining suitability indices of each instrument in the plurality of instruments based on each instrument's suitability to respond to an emergency of a duration specified in the plurality of real-time measurements.

14. The method of claim 7, wherein determining the plurality of suitability indices comprises determining suitability indices of each instrument in the plurality of instruments based on each instrument's suitability to respond to a spill having a spill rate and spill volume specified in the plurality of real-time measurements.

15. The method of claim 7, wherein determining the plurality of suitability indices comprises determining suitability indices of each instrument in the plurality of instruments based on each instrument's suitability to respond to a spill having an oil type specified in the plurality of real-time measurements, and wherein the oil type is light crude, heavy crude, or fuel oil.

16. The method of claim 7, wherein determining the plurality of suitability indices comprises determining suitability indices of each instrument in the plurality of instruments based on each instrument's suitability to respond to a spill having an oil condition specified in the plurality of real-time measurements, and wherein the oil condition is subsea or floating.

17. The method of claim 7, wherein determining the plurality of suitability indices comprises determining suitability indices of each instrument in the plurality of instruments based on each instrument's suitability to respond to a spill having an oil condition specified in the plurality of real-time measurements, and wherein the oil condition is slick or emulsion.

18. The method of claim 7, wherein determining the plurality of suitability indices comprises determining suitability indices of each instrument in the plurality of instruments based on each instrument's suitability to respond to a spill having an oil condition specified in the plurality of real-time measurements, and wherein the oil condition is mousse or tar.

19. The method of claim 7, wherein determining the plurality of suitability indices comprises determining suitability indices of each instrument in the plurality of instruments based on each instrument's suitability to respond to a spill type specified in the plurality of real-time measurements.

20. A method, comprising:
receiving a plurality of real-time measurements at a geographic location of an oil spill;
determining a plurality of performance scores for a plurality of instruments for an oil spill response, wherein determining the plurality of performance scores comprises:
determining availability, readiness, and ownership of each instrument in the plurality of instruments,
determining false positive and false negative potential of each instrument in the plurality of instruments,
determining a degree of automation of each instrument in the plurality of instruments,
determining latency of each instrument in the plurality of instruments, and
determining mounting requirements of each instrument in the plurality of instruments;
determining a plurality of suitability indices for the plurality of instruments, wherein determining the plurality of suitability indices comprises:
evaluating each instrument in the plurality of instruments based on parameters from a prior emergency, parameters from a simulated emergency, and parameters from the plurality of real-time measurements,
determining suitability indices of each instrument in the plurality of instruments based on each instrument's suitability to respond to an emergency of a duration specified in the plurality of real-time measurements,
determining suitability indices of each instrument in the plurality of instruments based on each instrument's suitability to respond to a spill having a spill rate and spill volume specified in the plurality of real-time measurements,
determining suitability indices of each instrument in the plurality of instruments based on each instrument's suitability to respond to a spill having an oil type specified in the plurality of real-time measurements,
determining suitability indices of each instrument in the plurality of instruments based on each instrument's suitability to respond to a spill having an oil condition specified in the plurality of real-time measurements, and
determining suitability indices of each instrument in the plurality of instruments based on each instrument's suitability to respond to a spill type specified in the plurality of real-time measurements; and
determining respective instrument ratings for the plurality of instruments based on the performance scores and the suitability indices for each instrument.

* * * * *